(12) United States Patent
Hara

(10) Patent No.: US 10,945,749 B2
(45) Date of Patent: Mar. 16, 2021

(54) MANIPULATOR

(71) Applicant: OLYMPUS CORPORATION, Tokyo (JP)

(72) Inventor: Mitsuhiro Hara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 371 days.

(21) Appl. No.: 15/980,838

(22) Filed: May 16, 2018

(65) Prior Publication Data

US 2018/0256183 A1    Sep. 13, 2018

Related U.S. Application Data

(63) Continuation of application No. PCT/JP2016/050965, filed on Jan. 14, 2016.

(51) Int. Cl.
*A61B 17/29* (2006.01)
*A61B 34/00* (2016.01)
(Continued)

(52) U.S. Cl.
CPC .............. *A61B 17/29* (2013.01); *A61B 18/04* (2013.01); *A61B 18/085* (2013.01); *A61B 18/1445* (2013.01); *A61B 34/30* (2016.02); *A61B 34/70* (2016.02); *A61B 34/71* (2016.02); *A61B 18/1442* (2013.01); *A61B 2017/00398* (2013.01); *A61B 2017/2932* (2013.01); *A61B 2017/2939* (2013.01); *A61B 2018/00994* (2013.01); *A61B 2018/126* (2013.01)

(58) Field of Classification Search
CPC .... A61B 2017/2905; A61B 2017/2932; A61B 2017/2939; A61B 18/1442; A61B 18/1445; A61B 34/30; A61B 34/70; A61B 34/71
See application file for complete search history.

(56) References Cited

U.S. PATENT DOCUMENTS

| 5,454,378 A | 10/1995 | Palmer et al. |
| 5,507,773 A | 4/1996 | Huitema et al. |

(Continued)

FOREIGN PATENT DOCUMENTS

| EP | 0668057 A2 | 8/1995 |
| EP | 0800792 A1 | 10/1997 |

(Continued)

OTHER PUBLICATIONS

International Search Report dated Feb. 23, 2016 issued in PCT/JP2016/050965.

*Primary Examiner* — Ronald Hupczey, Jr.
*Assistant Examiner* — Bradford C. Blaise
(74) *Attorney, Agent, or Firm* — Scully, Scott, Murphy & Presser, P.C.

(57) ABSTRACT

A manipulator includes: an elongated body portion that can be inserted into a body; and an energy treatment mechanism provided at a distal end of the body portion. The energy treatment mechanism is provided with gripping pieces that can grip body tissue and an energy applying part configured to apply energy to the body tissue gripped by the gripping pieces. The body portion is provided with an energy transfer part configured to transfer energy to the energy applying part and a force amplifying mechanism configured to amplify gripping force of the gripping pieces.

8 Claims, 12 Drawing Sheets

US 10,945,749 B2
Page 2

(51) Int. Cl.
 *A61B 34/30* (2016.01)
 *A61B 18/04* (2006.01)
 *A61B 18/08* (2006.01)
 *A61B 18/14* (2006.01)
 *A61B 18/00* (2006.01)
 *A61B 17/00* (2006.01)
 *A61B 18/12* (2006.01)

(56) References Cited

U.S. PATENT DOCUMENTS

| | | | |
|---|---|---|---|
| 5,553,624 | A | 9/1996 | Francese et al. |
| 5,562,700 | A | 10/1996 | Huitema et al. |
| 5,562,701 | A | 10/1996 | Huitema et al. |
| 5,562,702 | A | 10/1996 | Huitema et al. |
| 7,422,592 | B2 | 9/2008 | Morley et al. |
| 2003/0018331 | A1* | 1/2003 | Dycus ............... A61B 18/1445 606/48 |
| 2006/0217697 | A1 | 9/2006 | Lau et al. |
| 2011/0251608 | A1* | 10/2011 | Timm ................ A61B 17/295 606/41 |
| 2011/0257643 | A1 | 10/2011 | Lau et al. |
| 2013/0018373 | A1 | 1/2013 | Lau et al. |
| 2013/0046337 | A1* | 2/2013 | Evans ................. A61B 17/29 606/205 |
| 2014/0194876 | A1 | 7/2014 | Lau et al. |
| 2015/0164575 | A1 | 6/2015 | Lau et al. |
| 2017/0156782 | A1 | 6/2017 | Lau et al. |

FOREIGN PATENT DOCUMENTS

| | | |
|---|---|---|
| JP | 108033628 A | 2/1996 |
| JP | 2005512606 A | 5/2005 |
| JP | 2005193061 A | 7/2005 |
| JP | 2008534069 A | 8/2008 |
| JP | 2010259479 A | 11/2010 |
| WO | 2002080799 A1 | 10/2002 |
| WO | 2006104836 A2 | 10/2006 |

\* cited by examiner

MANIPULATOR

CROSS-REFERENCE TO RELATED APPLICATIONS

This is a Continuation Application of International Application No. PCT/JP2016/050965 filed on Jan. 14, 2016, the content of which is incorporated herein by reference in its entirety.

TECHNICAL FIELD

The present invention relates to a manipulator.

BACKGROUND ART

In the related art, there is a known manipulator that is provided with a gripping mechanism for gripping an object, such as body tissue, and that applies energy treatment to the object gripped by the gripping mechanism (for example, see PTL 1). The manipulator described in PTL 1 is provided with a gripping structure in which a bipolar electrode is provided at the distal end of a wrist mechanism of a surgical instrument that is inserted into a living body and with which robotic surgery is performed.

CITATION LIST

Patent Literature

{PTL 1} U.S. Pat. No. 7,422,592

SUMMARY OF INVENTION

One aspect the present disclosure is a manipulator comprising: an insertion portion that can be inserted into a body; and an energy treatment mechanism that is provided at a distal end of the insertion portion, wherein the energy treatment mechanism is provided with a gripper that can grip body tissue and an energy applying part configured to apply energy to the body tissue gripped by the gripper; and the insertion portion is provided with an energy transfer part configured to transfer energy to the energy applying part and a force amplifying mechanism configured to amplify gripping force of the gripper.

DESCRIPTION OF EMBODIMENTS

First Embodiment

A manipulator according to a first embodiment of the present invention will be described below with reference to the drawings.

Figure 1:
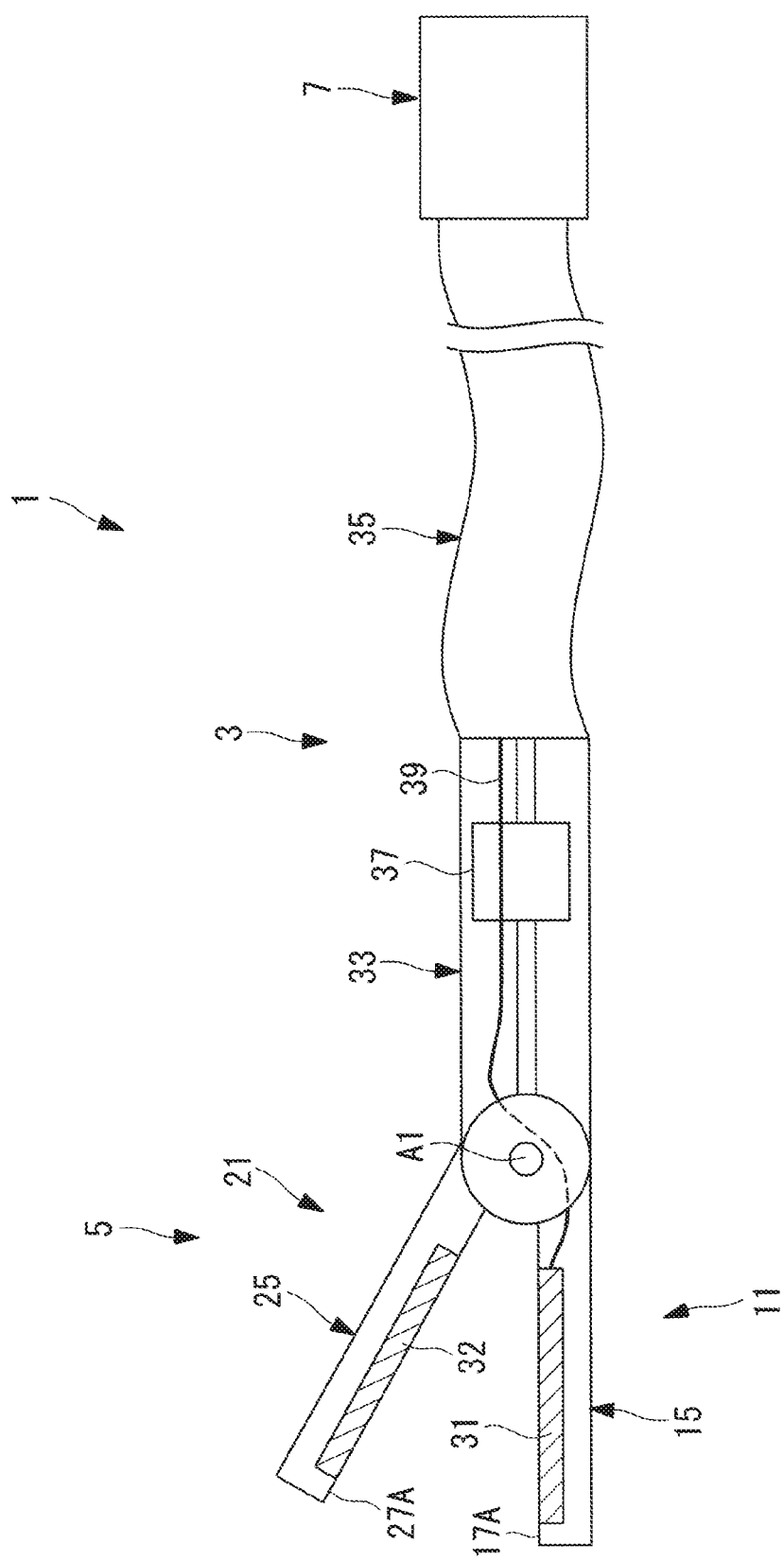
FIG. 1 is a view showing the overall configuration of a manipulator according to a first embodiment of the present invention.

As shown in FIG. 1, for example, a manipulator 1 of this embodiment is a medical instrument having a function of gripping body tissue, as in grasping forceps. The manipulator 1 is provided with: an elongated body portion (insertion portion) 3 that can be inserted into a body; an energy treatment mechanism 5 that is provided at the distal end of the body portion 3; and a drive unit 7 that is connected to the proximal end of the body portion 3.

The energy treatment mechanism 5 is provided with: an elongated first gripping piece 11 and an elongated second gripping piece 21 (each of which is a gripper, jaw) that can grip body tissue; and energy applying parts 31 and 32 that apply thermal energy to the body tissue gripped by the first gripping piece 11 and the second gripping piece 21.

Figure 2:
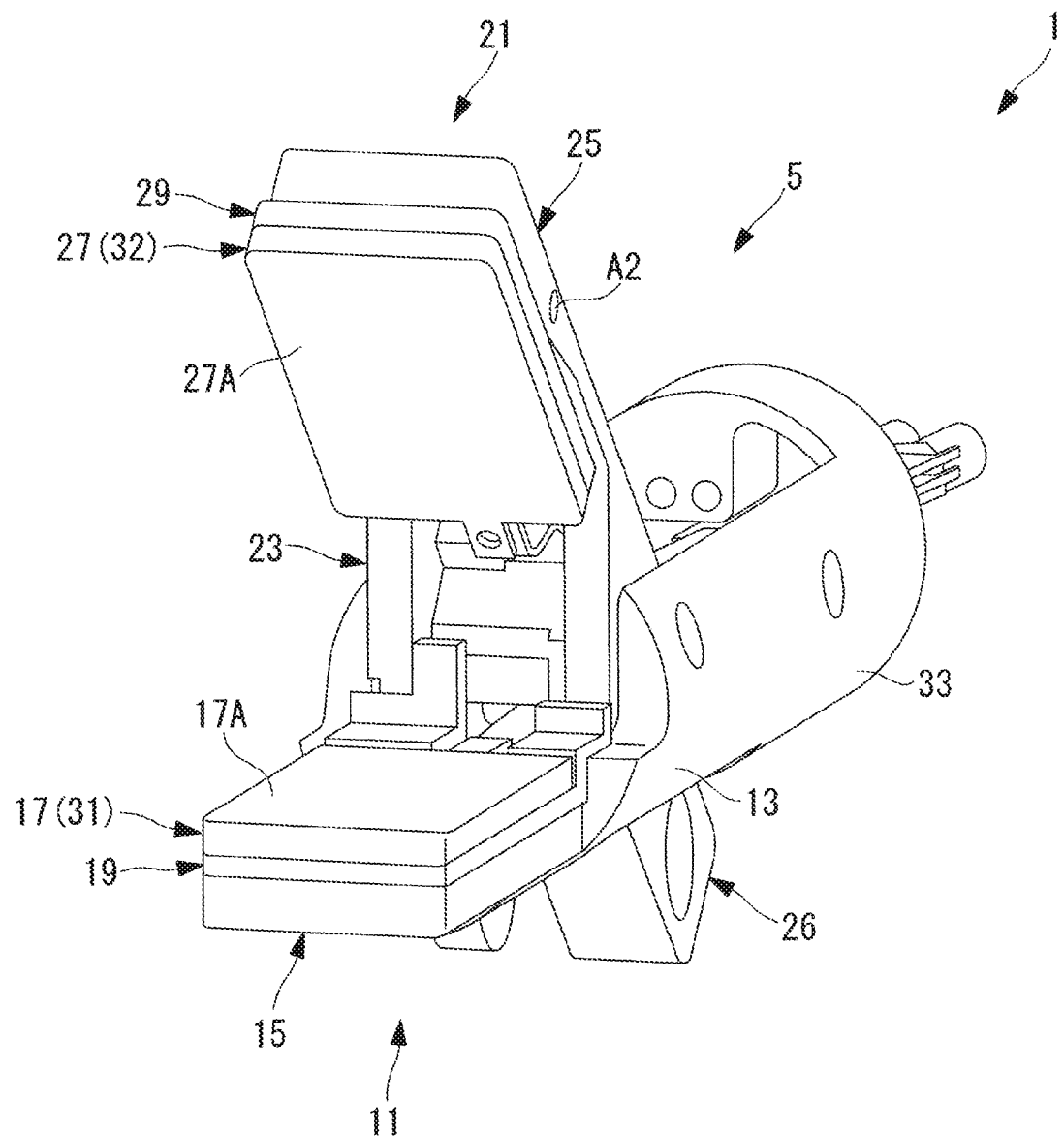
FIG. 2 is a perspective view of an energy treatment mechanism shown in FIG. 1, viewed from the distal end thereof.

As shown in FIG. 2, the first gripping piece 11 and the second gripping piece 21 have a single-pivot gripping mechanism in which the first gripping piece 11 is not capable of pivoting, and the second gripping piece 21 is capable of pivoting. The first gripping piece 11 is provided with: a first coupling part 13 that is formed integrally with the body portion 3; and a substantially flat-plate shaped first gripping part 15 that extends from the first coupling part 13 in the longitudinal direction.

The first gripping part 15 is provided with: a first blade 17 that has a first gripping surface 17A; and a first thermal-insulating member 19 that insulates the first gripping part 15 from the heat from the first blade 17. The first blade 17 and the first thermal-insulating member 19 are each formed into a flat-plate shape, and the first thermal-insulating member 19 and the first blade 17 are disposed in this order on the first gripping part 15 in a laminated manner.

The second gripping piece 21 is provided with: a second coupling part 23 that is coupled to the first coupling part 13 of the first gripping piece 11; a substantially flat-plate shaped second gripping part 25 that extends from the second coupling part 23 in one longitudinal direction; and a second proximal-end part 26 that extends from the second coupling part 23 in the other longitudinal direction.

The second gripping part 25 is provided with: a second blade 27 that has a second gripping surface 27A; and a second thermal-insulating member 29 that insulates the second gripping part 25 from the heat from the second blade 27. The second blade 27 and the second thermal-insulating member 29 are each formed into a flat-plate shape, and the second thermal-insulating member 29, and the second blade 27 are disposed in this order on the second gripping part 25 in a laminated manner. Although an example case in which the first blade 17 and the second blade 27 are each formed into a flat-plate shape is shown here, the gripping surfaces of the first blade 17 and the second blade 27 may be formed into a convex shape in order to enhance the incision performance of the gripped tissue.

The second coupling part 23 is coupled to the first coupling part 13 of the first gripping piece 11 by means of a hinge (not shown) so as to be capable of pivoting about an opening/closing pivot shaft A1 (see FIG. 1) perpendicular to the longitudinal axis of the body portion 3. The first gripping part 15 of the first gripping piece 11 and the second gripping part 25 of the second gripping piece 21 are disposed parallel to the direction along the longitudinal axis of the body portion 3, with the first gripping surface 17A and the second gripping surface 27A being opposed to each other.

Furthermore, the second coupling part 23 of the second gripping piece 21 is made to pivot about the opening/closing pivot shaft A1, thus causing the first gripping part 15 of the first gripping piece 11 and the second gripping part 25 of the second gripping piece 21 to open and close relative to each other. Hereinafter, the arrangement direction of the first gripping part 15 of the first gripping piece 11 and the second gripping part 25 of the second gripping piece 21 is defined as vertical direction, the first gripping part 15 of the first gripping piece 11 is defined to be on a lower side, and the second gripping part 25 of the second gripping piece 21 is defined to be on an upper side.

Figure 3:
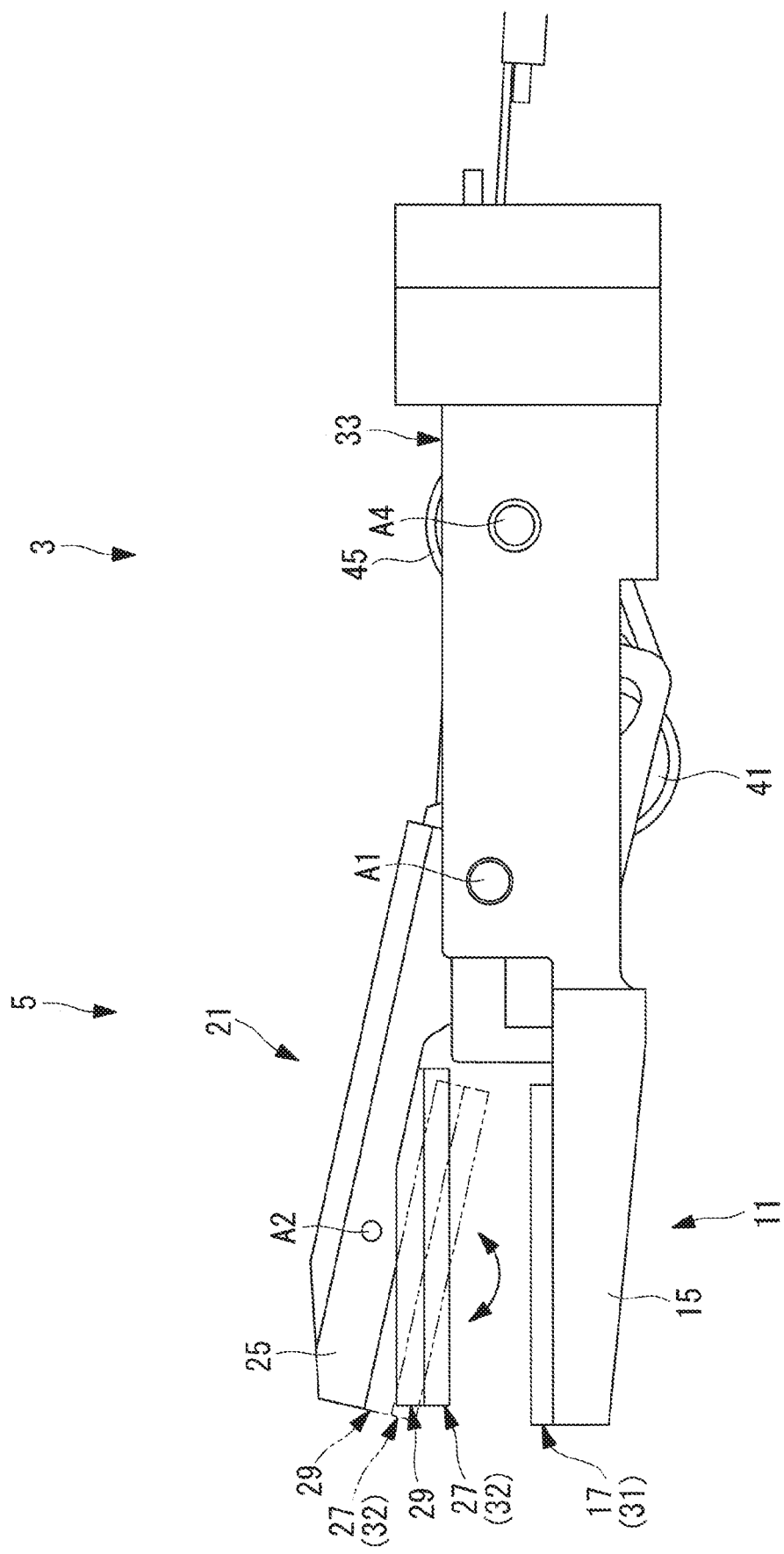
FIG. 3 is a side view of the energy treatment mechanism and a body portion shown in FIG. 1, viewed from a direction perpendicular to the longitudinal axis thereof.

Furthermore, as shown in FIG. 3, the second blade 27 and the second thermal-insulating member 29 are provided in the second gripping part 25 so as to be capable of swinging about an inclined swing shaft A2 parallel to the opening/closing pivot shaft A1. The second blade 27 and the second thermal-insulating member 29 are made to swing about the inclined swing shaft A2 to change the inclinations thereof, thereby making it possible to cause the second gripping surface 27A to be opposed to the first gripping surface 17A substantially parallel thereto even in a state in which the second gripping part 25 of the second gripping piece 21 is open with respect to the first gripping part 15 of the first gripping piece 11.

Figure 4:
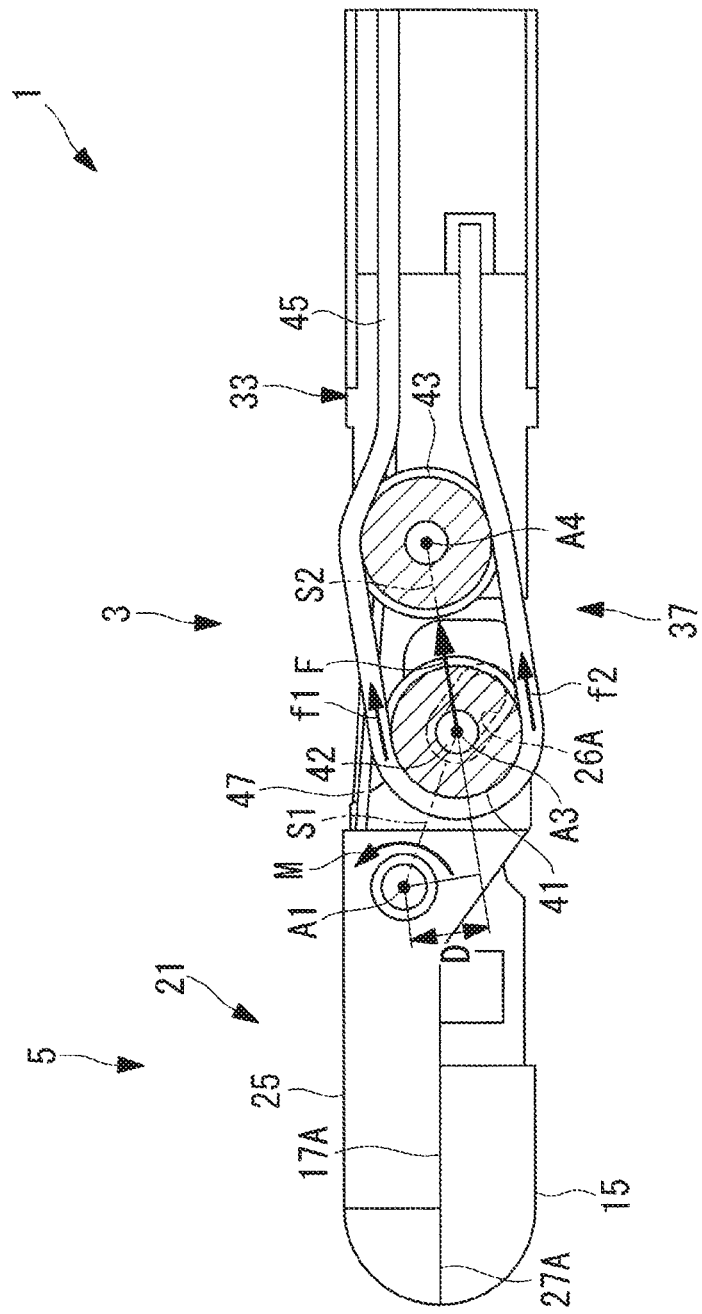
FIG. 4 is a longitudinal sectional view of the energy treatment mechanism and the body portion shown in FIG. 3.
Figure 5:
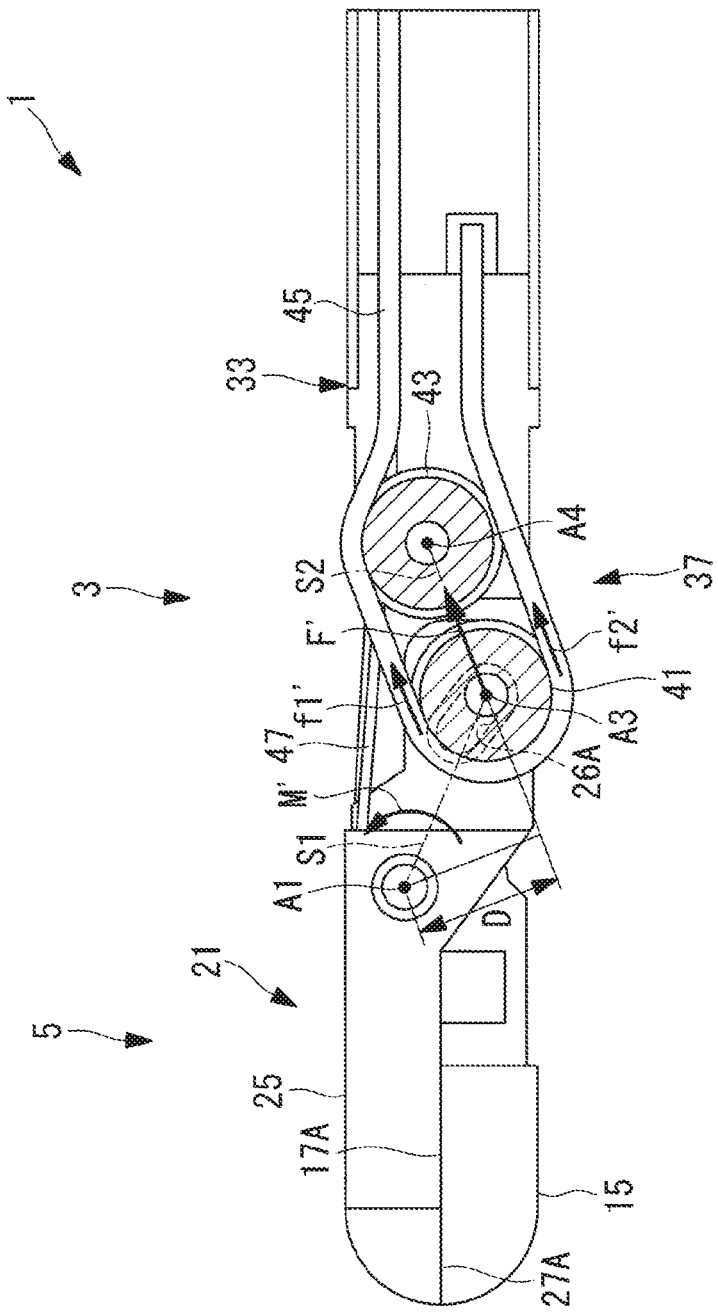
FIG. 5 is a longitudinal sectional view showing a state in which a closing wire shown in FIG. 3 is pulled toward the proximal end thereof.

As shown in FIGS. 4 and 5, a slit 26A that has a depth in a direction parallel to the opening/closing pivot shaft A1 is formed in the second proximal-end part 26. The slit 26A is formed so as to extend substantially in a radial direction farther toward the proximal end of the body portion 3 and downward thereof than the opening/closing pivot shaft A1 is.

As shown in FIG. 1, the energy applying parts 31 and 32 are heat transfer parts that contain heat generation chips, and are formed of heat resistances, such as copper wires, for example. The energy applying parts 31 and 32 are each formed into a sheet shape and are respectively embedded in the first blade 17 of the first gripping part 15 and the second blade 27 of the second gripping part 25 along the longitudinal directions of the first gripping surface 17A and the second gripping surface 27A. The energy applying part that is embedded in the first blade 17 is denoted by reference numeral 31, and the energy applying part that is embedded in the second blade 27 is denoted by reference numeral 32.

The energy applying parts 31 and 32 are heated to 100° C. to 400° C., for example. Furthermore, the energy applying parts 31 and 32 are embedded in the blades 17 and 27, respectively, the thermal-insulating member 19 is disposed between the blade 17 and the gripping part 15, and the thermal-insulating member 29 is disposed between the blade 27 and the gripping part 25, thus making it possible to efficiently transfer thermal energy from the energy applying parts 31 and 32 to the gripping surfaces 17A and 27A, respectively, and to locally apply energy treatment to a region of the body tissue gripped between the gripping surfaces 17A and 27A.

The body portion 3 is provided with: a cylindrical outer tube part 33; and an elongated flexible part 35 that is connected to the proximal end of the outer tube part 33 and that has flexibility.

The outer tube part 33 is provided with: a force amplifying mechanism 37 that amplifies the gripping force of the gripping pieces 11 and 21; and energy transfer parts 39 and 40 that transfer thermal energy to the energy applying parts 31 and 32.

Figure 6:
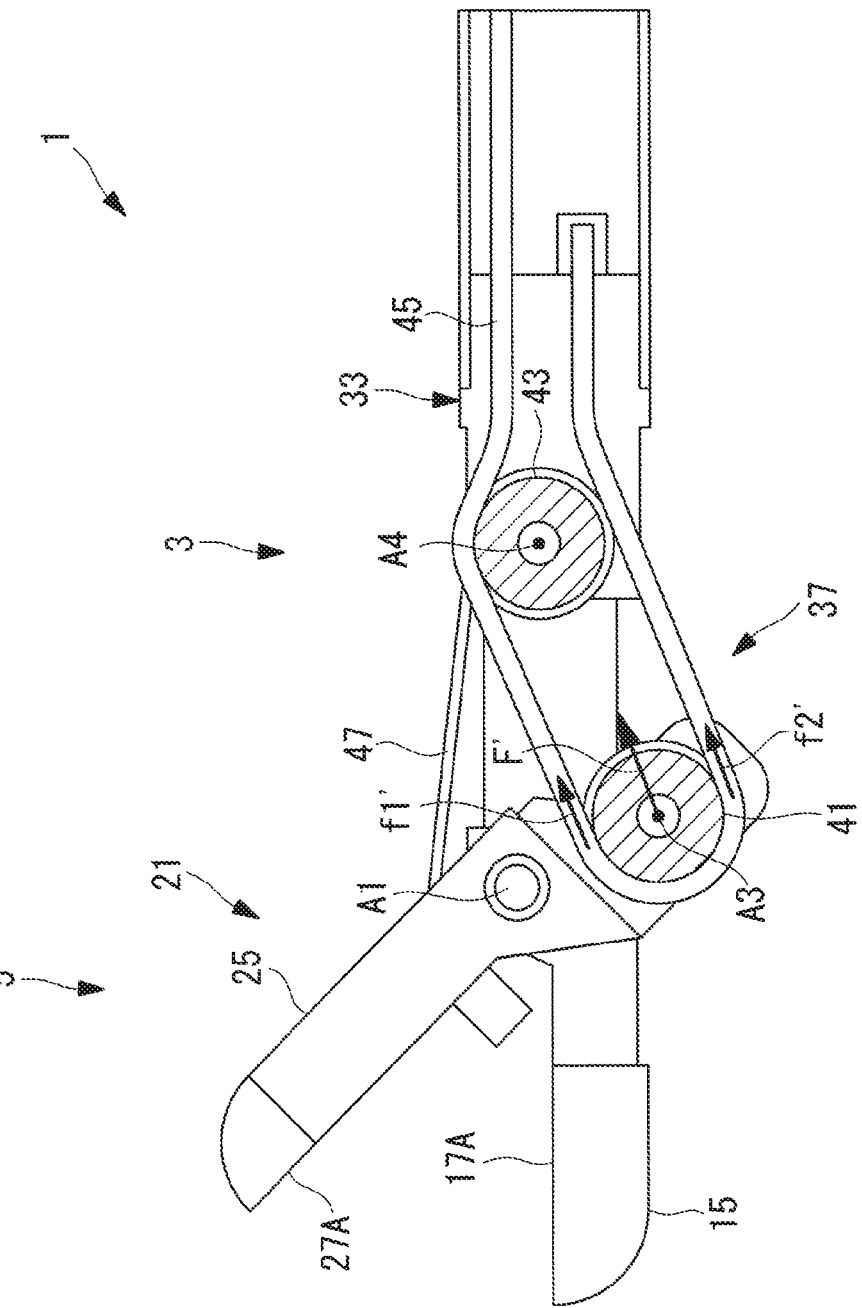
FIG. 6 is a longitudinal sectional view showing a state in which a first gripping piece and a second gripping piece shown in FIG. 3 are open.

As shown in FIGS. 4 to 6, the force amplifying mechanism 37 is provided with: a pulling pulley (pulley) 41 that is supported by the second coupling part 23 of the second gripping piece 21; an adjustment pulley (pulley) 43 that is supported by the outer tube part 33; and a closing wire (pulling-force transfer unit) 45 that causes the second gripping piece 21 to produce the gripping force, via the pulling pulley 41 and the adjustment pulley 43. An opening wire 47 is connected to the second gripping part 25.

The pulling pulley 41 has a shaft 42 disposed coaxially with a pulling rotational axis A3 of the pulling pulley 41. The pulling pulley 41 is supported by the second proximal-end part 26 of the second gripping piece 21 such that, when the shaft 42 is inserted into the slit 26A, which is formed in the second coupling part 23 of the second gripping piece 21, the pulling pulley 41 is capable of rotating about the pulling rotational axis A3, which is parallel to the opening/closing pivot shaft A1, and is also capable of moving, along the longitudinal direction of the slit 26A, in directions toward and away from the opening/closing pivot shaft A1.

The adjustment pulley 43 is disposed closer to the proximal end of the body portion 3 than the pulling pulley 41 is and is provided in a rotatable manner about an adjustment rotational axis A4 that is parallel to the pulling rotational axis A3. The adjustment pulley 43 can adjust the direction of the closing wire 45, which extends from an upper end of the pulling pulley 41 to the proximal end of the body portion 3.

The closing wire 45 is wired inside the body portion 3 in the longitudinal direction thereof and is wound, via the adjustment pulley 43, around only about half of the outer peripheral surface of the pulling pulley 41, said half being close to the distal end of the body portion 3. Furthermore, the distal end section of the closing wire 45 is made to return by the pulling pulley 41 and is fixed to the body portion 3 at a position closer to the proximal end than the adjustment pulley 43 is, and the proximal end section of the closing wire 45 is fixed to the drive unit 7. A section of the closing wire 45 extending from the lower end of the pulling pulley 41 to the lower end of the adjustment pulley 43 and a section of the closing wire 45 extending from the upper end of the pulling pulley 41 to the upper end of the adjustment pulley 43 are disposed substantially parallel to each other.

As shown in FIG. 5, in the force amplifying mechanism 37, the adjustment pulley 43 is provided so as to change the direction of the resultant force F' of a tension f1' and a tension f2' to the direction in which a distance D' is increased, i.e., the direction in which a rotational moment M' is increased.

Figure 7:
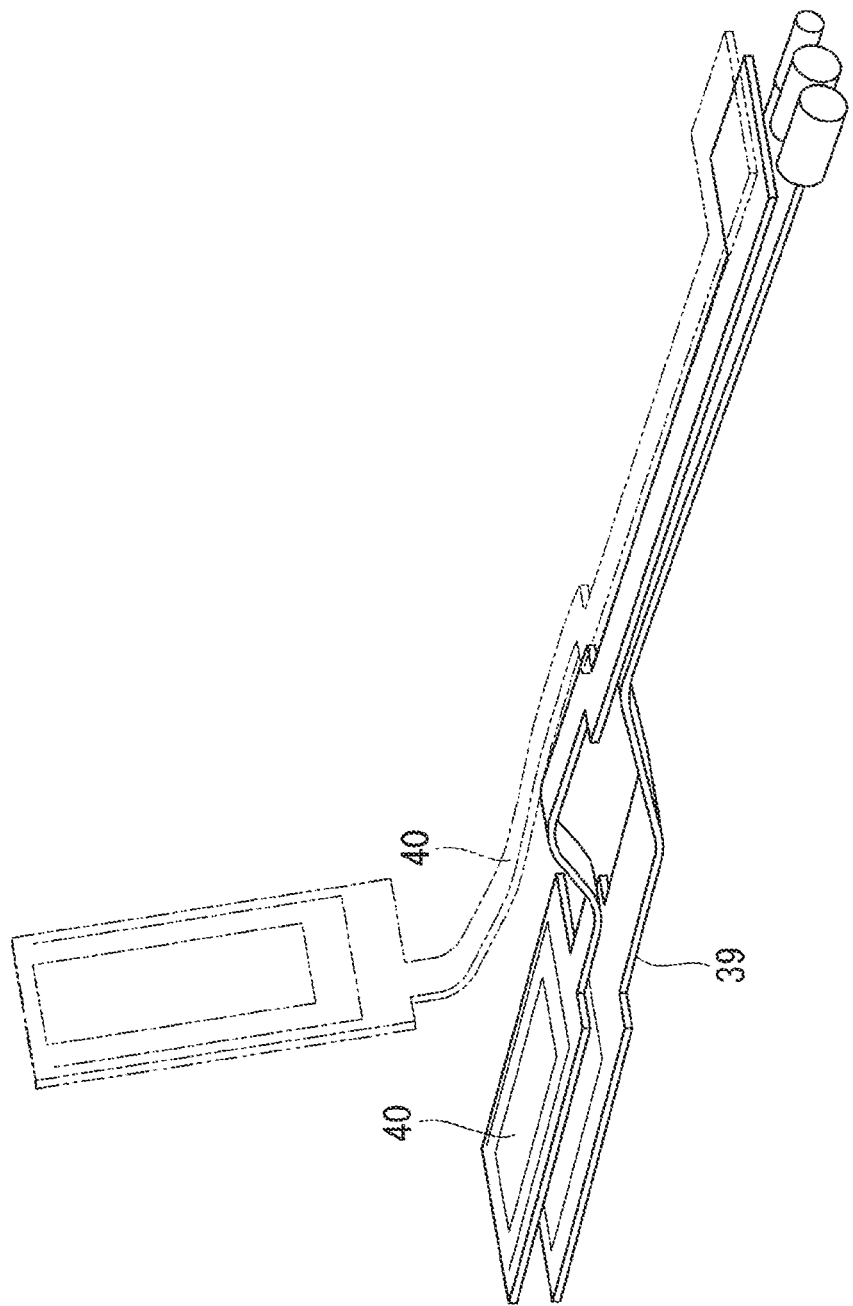
FIG. 7 is a perspective view showing flexible substrates of energy transfer parts shown in FIG. 1.

As shown in FIGS. 1 and 7, for example, sections of the energy transfer parts 39 and 40 between the energy applying parts 31 and 32 and the force amplifying mechanism 37 are conducting wires formed of flexible substrates. The energy transfer part that is connected to the energy applying part 31 is denoted by reference numeral 39, and the energy transfer part that is connected to the energy applying part 32 is denoted by reference numeral 40. Furthermore, the energy transfer parts 39 and 40 are each disposed so as to be distant from the force amplifying mechanism 37 in the width direction of the body portion 3, so as not to interfere with the force amplifying mechanism 37.

Figure 8:
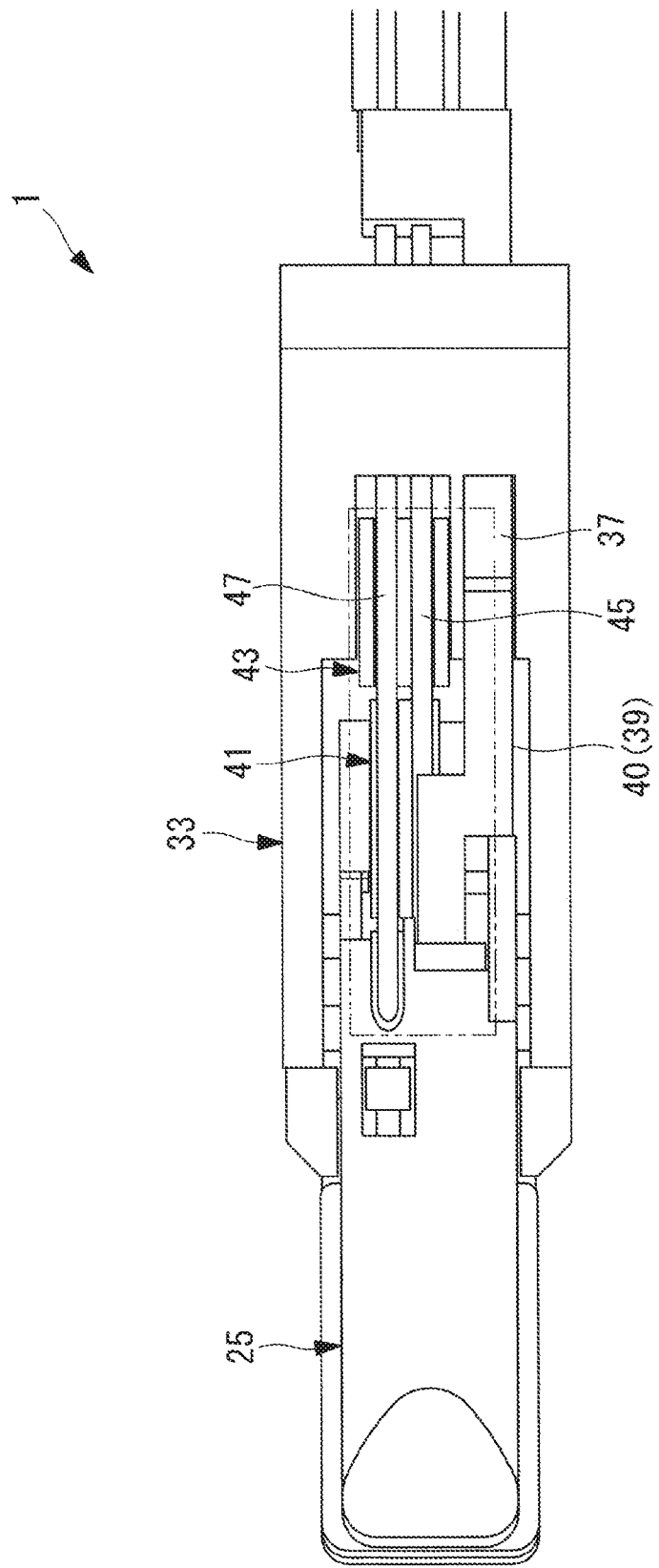
FIG. 8 is a plan view of the energy treatment mechanism and the body portion shown in FIG. 1, viewed from the top.

Specifically, as shown in FIG. 8, the energy transfer parts 39 and 40 are bent in a crank shape in the direction along the rotational axes A3 and A4 of the pulling pulley 41 and the adjustment pulley 43, so as to avoid the force amplifying mechanism 37. By doing so, it is possible to efficiently prevent interference between the energy transfer parts 39 and 40 and the force amplifying mechanism 37 and to eliminate a waste of the space, thus achieving a reduction in the diameter of the body portion 3.

Figure 9:
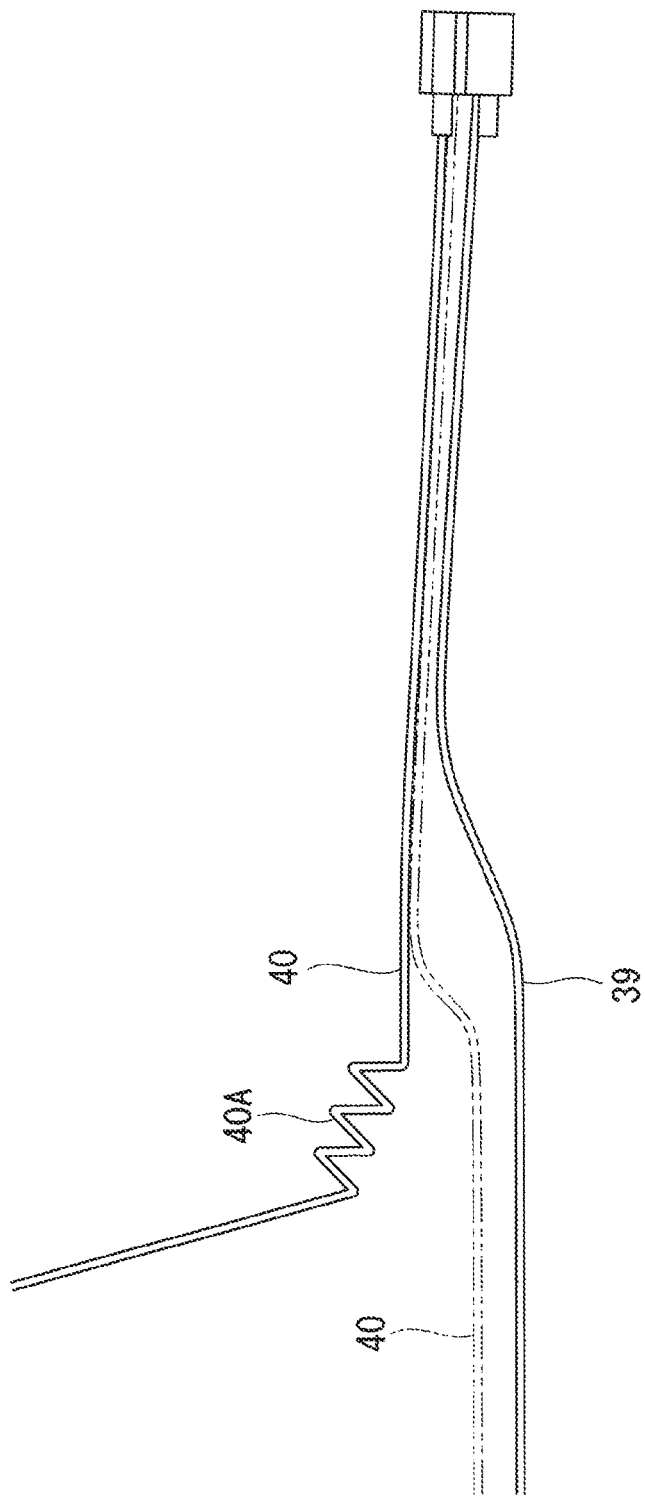
FIG. 9 is a side view showing the flexible substrates of the energy transfer parts shown in FIG. 7.

Furthermore, as shown in FIG. 9, the energy transfer part 40, which is connected to the energy applying part 32 of the second gripping piece 21, has a bellows-shaped expansion and contraction section 40A that can expand and contract in the longitudinal direction of the body portion 3 in accordance with the opening/closing operation of the first gripping piece 11 and the second gripping piece 21. For example, the expansion and contraction section 40A is formed in the energy transfer part 40 in the vicinity of a point between the body portion 3 and the energy treatment mechanism 5, i.e., in the vicinity of the opening/closing pivot shaft A1.

Although the flexible substrate of the energy transfer part 39, which is connected to the first gripping part 15, does not move in the longitudinal direction of the body portion 3 even when the gripping pieces 11 and 21 are opened or closed, the flexible substrate of the energy transfer part 40, which is connected to the second gripping part 25, moves in the longitudinal direction of the body portion 3 when the gripping pieces 11 and 21 are opened or closed.

Since the energy transfer part 40 has the expansion and contraction section 40A, so that the expansion and contraction section 40A can absorb displacement of the flexible substrate in the longitudinal direction of the body portion 3 caused in accordance with the gripping operation of the gripping pieces 11 and 21, it is possible to prevent the gripping operation of the gripping pieces 11 and 21 from being disturbed by the displacement of the flexible substrate of the energy transfer part 40.

As shown in FIG. 1, because the flexible part 35 is inserted into a narrow region, such as lumen, the outer diameter thereof is set to be small, about 3 mm. The wires 45 and 47 for opening and closing the gripping pieces 11 and 21 and the energy transfer parts 39 and 40 for transferring thermal energy to the energy applying parts 31 and 32 pass through the flexible part 35.

The drive unit 7 has a motor (not shown) to which the proximal ends of the wires 45 and 47 are connected, so that the wires 45 and 47 are selectively pulled toward the proximal ends thereof through actuation of the motor, thus causing tensions to be produced selectively on the wires 45 and 47.

The operation of the thus-configured manipulator 1 will now be described.

In order to apply energy treatment to body tissue in the body of a patient by using the manipulator 1 of this embodiment, the energy treatment mechanism 5 and the body portion 3 are inserted into the body, and, as shown in FIGS. 4 to 6, the opening wire 47 and the closing wire 45 are alternately pulled, thereby gripping target body tissue through the opening/closing operation of the gripping pieces 11 and 21 of the energy treatment mechanism 5.

Specifically, the drive unit 7 is actuated to open the gripping pieces 11 and 21, as shown in FIG. 6, and then to pull the closing wire 45 toward the proximal end, thus producing, at upper and lower sides of the pulling pulley 41, as shown in FIG. 4, tensions f1 and f2 that are in almost the same direction toward the proximal end and that have substantially the same magnitudes as the pulling force, which is applied to the proximal end portion of the closing wire 45 by the drive unit 7.

The pulling pulley 41 is pulled toward the proximal end by the resultant force F=f1+f2 of the tension f1 and the tension f2, thus being moved from the position in the slit 26A closest to the distal end, as shown in FIG. 4, to the position in the slit 26A closest to the proximal end, as shown in FIG. 5, in the direction away from the opening/closing pivot shaft A1.

In the state in which the pulling pulley 41 has been moved to the position in the slit 26A closest to the proximal end, tensions f1' and f2' in almost the same direction toward the proximal end of the body portion 3 are produced on the closing wire 45 at both upper and lower sides of the pulling pulley 41, as shown in FIG. 5. Accordingly, the resultant force F'=f1'+f2' of the tension f1' and the tension f2' acts on the pulling pulley 41. Specifically, the pulling force applied to the proximal end portion of the closing wire 45 is amplified by a factor of two and then acts on the pulling pulley 41. Then, the resultant force F' also acts on the second gripping piece 21, which supports the pulling pulley 41.

Here, the resultant force F' acting on the pulling rotational axis A3 of the pulling pulley 41, which is located lower with respect to the opening/closing pivot shaft A1, acts in a direction intersecting with a line segment S1 that connects the opening/closing pivot shaft A1 and the pulling rotational axis A3. Therefore, the resultant force F' produces a component in the tangent direction about the opening/closing pivot shaft A1, i.e., rotational moment M' that causes the second gripping part 25 to pivot about the opening/closing pivot shaft A1 in the closing direction. Accordingly, the second gripping part 25 is pressed against the first gripping part 15, and the body tissue is sandwiched between the first gripping surface 17A of the first gripping piece 11 and the second gripping surface 27A of the second gripping piece 21 and is gripped therebetween.

In this case, the pulling force is amplified by a factor of two by the pulling pulley 41, thereby making it possible to increase the rotational moment M' by about two-times and to increase the gripping force of the gripping pieces 11 and 21 by about two-times, compared with a structure in which the second gripping piece 21 is pulled by a single wire, for example.

After the body tissue is gripped by the gripping pieces 11 and 21, the energy applying parts 31 and 32 apply, to the body tissue, thermal energy transmitted by the energy transfer parts 39 and 40. Accordingly, it is possible to apply energy treatment to the body tissue gripped by the gripping pieces 11 and 21.

As described above, according to the manipulator 1 of this embodiment, the force amplifying mechanism 37 amplifies the pulling force applied from the drive unit 7 to the closing wire 45 by a factor of about two, to amplify the gripping force of the gripping pieces 11 and 21 by a factor of about two, thus making it possible to apply energy treatment in a state in which the body tissue is stably gripped with sufficient gripping force.

This embodiment can be modified as follows.

Figure 10:
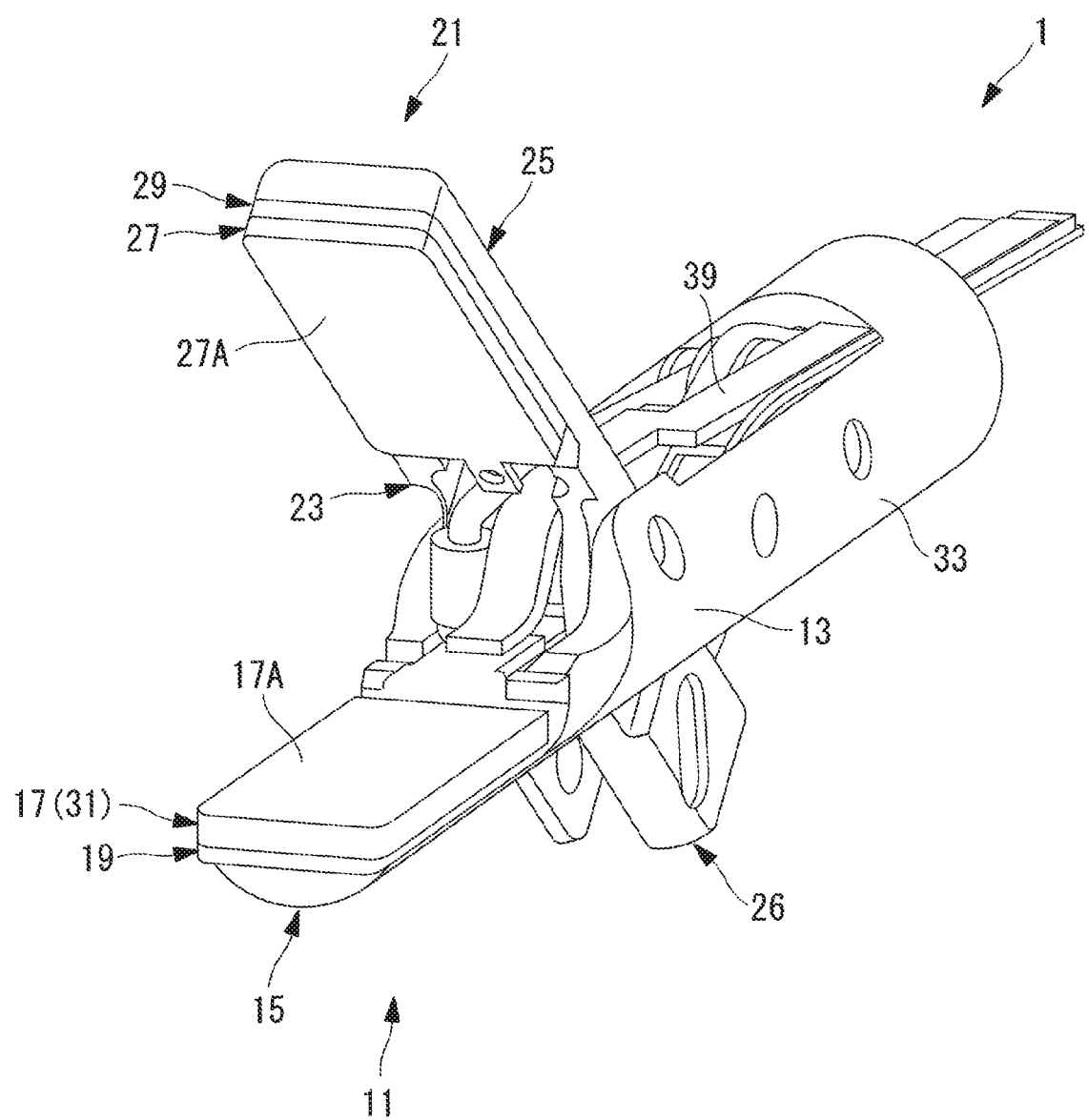
FIG. 10 is a perspective view of an energy treatment mechanism and a body portion of a manipulator according to one modification of the first embodiment of the present invention, viewed from the distal end thereof.

In this embodiment, although the energy applying parts 31 and 32 are provided on the gripping pieces 11 and 21, in one modification, it is also possible to provide an energy applying part on only one of the gripping pieces 11 and 21. FIG. 10 shows an example case in which the energy applying part 32 is not provided, and the energy applying part 31 is embedded only in the first blade 17 of the first gripping piece 11.

According to this modification, because the energy transfer part 40, which is connected to the energy applying part 32, need not be provided, either, it is unnecessary to consider displacement of the flexible substrate in the longitudinal direction of the body portion 3 caused in accordance with the opening/closing operation of the gripping pieces 11 and 21. In FIG. 10, in order to reduce the size of the manipulator 1, the second gripping part 25 is not provided with the inclined swing shaft A2, so that the second blade 27 and the second thermal-insulating member 29 do not swing.

Second Embodiment

Next, a manipulator according to a second embodiment of the present invention will be described.

Figure 11:
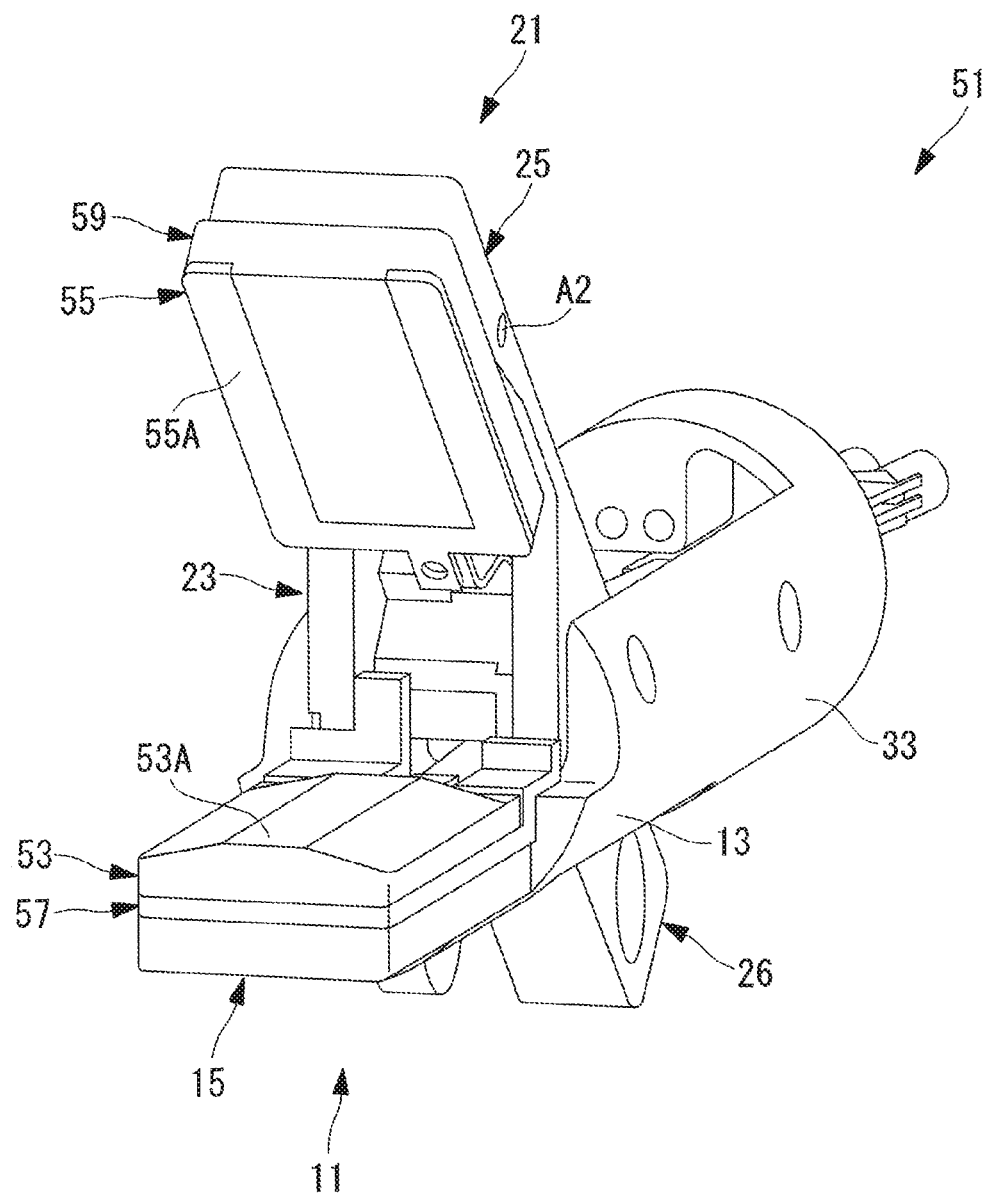
FIG. 11 is a perspective view of an energy treatment mechanism and a body portion of a manipulator according to a second embodiment of the present invention, viewed from the distal end thereof.

A manipulator 51 of this embodiment is a bipolar-type energy-treatment manipulator, as shown in FIG. 11. The manipulator 51 differs from that in the first embodiment in that energy applying parts 53 and 55 that are formed of metal high-frequency electrodes for applying bipolar high-frequency voltages are adopted instead of the energy applying parts 31 and 32, which are heat transfer parts containing heat generation chips.

Identical reference signs are assigned below to portions having configurations common to those in the manipulator 1 of the first embodiment, and a description thereof will be omitted.

The energy applying parts 53 and 55 are provided on the gripping parts 15 and 25 of the gripping pieces 11 and 21, respectively. Hereinafter, the energy applying part that is provided in the first gripping piece 11 is denoted by reference numeral 53, and the energy applying part that is provided in the second gripping piece 21 is denoted by reference numeral 55.

Instead of the blades 17 and 27 and the thermal-insulating members 19 and 29, the energy applying parts 53 and 55 are respectively provided in the gripping parts 15 and 25 via flat-plate-shaped insulating members 57 and 59 that are formed of insulating ceramic or resin, in a laminated manner. Hereinafter, the insulating member that is provided in the first gripping part 15 is referred to as the first insulating member 57, and the insulating member that is provided in the second gripping part 25 is referred to as the second insulating member 59. Furthermore, the energy applying parts 53 and 55 are connected, via the energy transfer parts 39 and 40, to a high-frequency energy output circuit (not shown) that is located close to the proximal end.

The energy applying part 53, which is provided in the first gripping part 15, is formed into a convex shape in which a center section thereof in the width direction protrudes in the lamination direction with respect to both sides thereof in the width direction, over the entire area thereof in the longitudinal direction. The center section of the energy applying part 53 forms a flat first gripping surface 53A that is opposed to the second gripping part 25.

The energy applying part 55, which is provided in the second gripping part 25, is formed into a U-shape. The second insulating member 59 has a stepped shape in which a center section thereof in the width direction protrudes in the thickness direction, a thin peripheral section thereof is laminated with the U-shaped energy applying part 55, and the thick center section thereof is located between electrodes of the U-shaped energy applying part 55. The thick center section of the second insulating member 59 and the peripheral U-shaped energy applying part 55 form a flat second gripping surface 55A that is opposed to the first gripping part 15.

Accordingly, when the first gripping part 15 and the second gripping part 25 are closed, the center section of the energy applying part 53 in the first gripping part 15 and the center section of the second insulating member 59 in the second gripping part 25 are brought into contact, and the high-frequency electrodes of the energy applying parts 53 and 55 are not brought into contact.

According to the manipulator 51 of this embodiment, in a state in which the force amplifying mechanism 37 amplifies the gripping force of the first gripping part 15 and the second gripping part 25, and body tissue is stably gripped, the energy applying parts 53 and 55 apply high-frequency energy output from the high-frequency energy output circuit, to the body tissue, thereby making it possible to incise and coagulate the body tissue.

Third Embodiment

Next, a manipulator according to a third embodiment of the present invention will be described.

Figure 12:
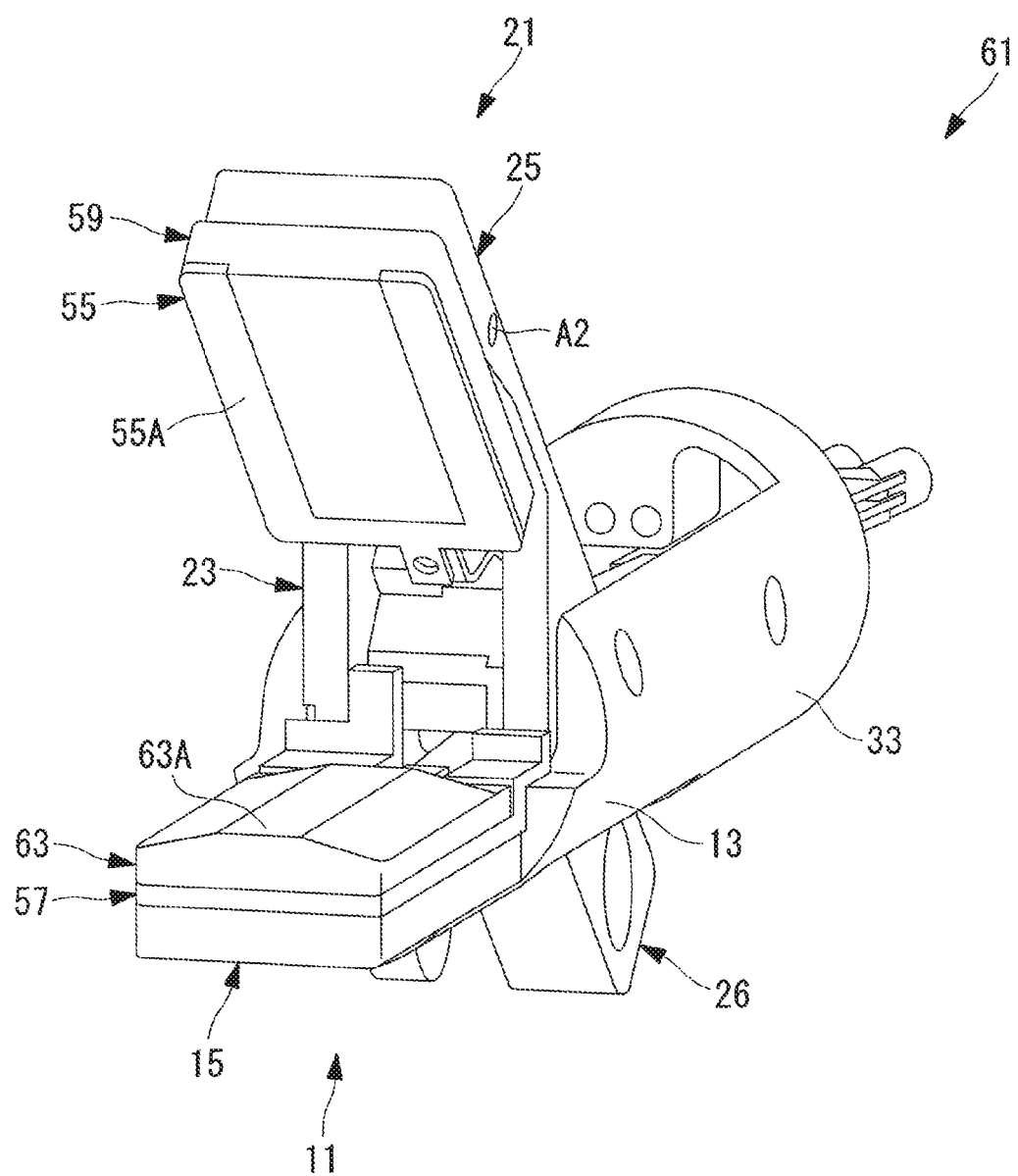
FIG. 12 is a perspective view of an energy treatment mechanism and a body portion of a manipulator according to a third embodiment of the present invention, viewed from the distal end thereof.

As shown in FIG. 12, a manipulator 61 of this embodiment differs from those in the first and second embodiments in that an energy applying part 63 that is formed of a heat transfer part containing a heat generation chip and a metal high-frequency electrode for applying a bipolar high-frequency voltage is adopted, instead of the energy applying part 31, 53.

Identical reference signs are assigned below to portions having configurations common to those in the manipulator 1, 51 of the first and second embodiments, and a description thereof will be omitted.

Instead of the blade 17 and the thermal-insulating member 19, the energy applying part 63 is provided in the first gripping part 15 via the flat-plate-shaped first insulating member 57, in a laminated manner. The heat transfer part of the energy applying part 63 is connected to a heat-resistance driving circuit via the energy transfer part 39, and the high-frequency electrode of the energy applying part 63 is connected to a high-frequency energy output unit via another energy transfer part 39.

The energy applying part 63 is formed into a convex shape in which a center section thereof in the width direction protrudes in the lamination direction with respect to both sides thereof in the width direction, over the entire area thereof in the longitudinal direction. The center section thereof in the width direction forms a flat first gripping surface 63A that is opposed to the second gripping part 25.

The second gripping part 25 is provided with the energy applying part 55, which is formed of a high-frequency electrode, and the second insulating member 59.

Accordingly, when the first gripping part 15 and the second gripping part 25 are closed, the center section of the energy applying part 63 in the first gripping part 15 and the center section of the second insulating member 59 in the second gripping part 25 are brought into contact, and the high-frequency electrodes of the energy applying parts 63 and 55 are not brought into contact.

According to the manipulator 61 of this embodiment, in a state in which the force amplifying mechanism 37 amplifies the gripping force of the first gripping part 15 and the second gripping part 25, and body tissue is stably gripped, the high-frequency electrodes of the energy applying parts 63 and 55 apply, to the body tissue, the high-frequency energy output from the high-frequency energy output circuit, and the heat transfer part of the energy applying part 63 applies, to the body tissue, the thermal energy transferred from the heat-resistance driving circuit, thereby making it possible to apply energy treatment to the body tissue. In this embodiment, the second gripping part 25 may also be provided with, instead of the energy applying part 55, an energy applying part that is formed of: a heat transfer part containing a heat generation chip; and a metal high-frequency electrode for applying a bipolar high-frequency voltage.

Although the embodiments of the present invention have been described above in detail with reference to the drawings, the specific configurations are not limited to those in the embodiments, and design changes etc. that do not depart from the scope of the present invention are also encompassed. For example, the present invention is not limited to the above-described embodiments and modification, can be applied to an embodiment obtained by appropriately combining the embodiments and the modification, and is not particularly limited.

Furthermore, in the above-described embodiments, although a mechanism using a moving pulley is shown as the force amplifying mechanism, instead of this, for example, it is also possible to adopt a mechanism in which the speed of rotation is reduced by a gear or a toggle mechanism in which a pair of links coupled in a rotatable manner about a rotational axis that is common to the gripping pieces 11 and 21 are opened and closed, thereby opening and closing the gripping pieces 11 and 21. Furthermore, in the above-described embodiments, although a heat transfer part that applies thermal energy or a high-frequency electrode that applies a bipolar high-frequency voltage is shown as the energy applying part, instead of this, for example, it is also possible to adopt a high-frequency electrode that applies a monopolar high-frequency voltage.

Furthermore, in the above-described embodiments, although a description has been given of the single-pivot gripping mechanism in which the first gripping piece 11 is not capable of pivoting, and the second gripping piece 21 is capable of pivoting, instead of this, it is also possible to adopt a single-pivot gripping mechanism in which the first gripping piece 11 is capable of pivoting, and the second gripping piece 21 is not capable of pivoting or a double-pivot gripping mechanism in which both the first gripping piece 11 and the second gripping piece 21 are capable of pivoting.

From the above-described embodiments, the following aspects of the present disclosure are derived.

One aspect the present disclosure is a manipulator comprising: an insertion portion that can be inserted into a body; and an energy treatment mechanism that is provided at a distal end of the insertion portion, wherein the energy treatment mechanism is provided with a gripper that can grip body tissue and an energy applying part configured to apply energy to the body tissue gripped by the gripper; and the insertion portion is provided with an energy transfer part configured to transfer energy to the energy applying part and a force amplifying mechanism configured to amplify gripping force of the gripper.

According to this aspect, the insertion portion is inserted into a body, and the energy applying part applies energy transferred by the energy transfer part, to the body tissue gripped by the grippers of the energy treatment mechanism, thereby making it possible to apply energy treatment to the body tissue gripped by the grippers. In this case, the force amplifying mechanism amplifies the gripping force of the grippers, thereby making it possible to apply the energy treatment in a state in which the body tissue is stably gripped with sufficient gripping force.

In the above-described aspect, the energy transfer part may be disposed away from the force amplifying mechanism in the width direction of the insertion portion.

With this configuration, the energy transfer part is prevented from interfering with the force amplifying mechanism, thus making it possible to smoothly operate the grippers.

In the above-described aspect, the energy transfer part may be bent in a crank shape so as to avoid the force amplifying mechanism.

With this configuration, it is possible to efficiently prevent interference between the energy transfer part and the force amplifying mechanism and to eliminate the waste of the space, thus achieving a reduction in the diameter of the insertion portion.

In the above-described aspect, the force amplifying mechanism may be provided with a pulling-force transfer unit configured to transfer pulling force to the gripper and a pulley configured to amplify the pulling force transferred by the pulling-force transfer unit.

With this configuration, amplification of the gripping force of the grippers can be realized, while achieving a reduction in the diameter of the insertion portion, with the simple structure formed of the pulling-force transfer unit and the pulley.

In the above-described aspect, the energy transfer part may be disposed at a position shifted with respect to the pulley so as not to overlap in the axial direction of the pulley.

With this configuration, the energy transfer part can be prevented from interfering with the operation of the pulley.

In the above-described aspect, the energy transfer part may have an expansion and contraction section configured to expand and contract in the longitudinal direction of the insertion portion in accordance with a gripping operation of the gripper.

With this configuration, displacement of the energy transfer part in the longitudinal direction of the insertion portion caused in accordance with the gripping operation of the grippers can be absorbed by the expansion and contraction section. Accordingly, it is possible to prevent the gripping operation of the grippers from being disturbed by displacement of the energy transfer part.

In the above-described aspect, the energy applying part may be disposed on a gripping surface of the gripper.

With this configuration, it is possible to locally apply energy treatment to a region, of the body tissue, gripped on the gripping surfaces of the grippers.

In the above-described aspect, the energy applying part may be formed into a sheet shape extending along the longitudinal direction of the insertion portion.

With this configuration, the energy applying part is brought into contact with the surface of the body tissue, thus making it possible to efficiently apply energy to the body tissue.

In the above-described aspect, the insertion portion is provided with a flexible part.

With this configuration, because the shape of the flexible part is made to change in accordance with the shape of a body cavity, the insertion portion can be smoothly inserted into the body cavity.

According to the aforementioned aspects, an advantageous effect is afforded in that it is possible to stably grip body tissue with sufficient gripping force and to apply energy treatment thereto.

REFERENCE SIGNS LIST 1, 51, 61 manipulator
3 body portion (insertion portion)
5 energy treatment mechanism
11 first gripping piece (gripper)
21 second gripping piece (gripper)
31, 32, 53, 55, 63 energy applying part
35 flexible part
37 force amplifying mechanism
39, 40 energy transfer part
40A expansion and contraction section
41 pulling pulley (pulley)
43 adjustment pulley (pulley)
45 wire (pulling-force transfer unit)

The invention claimed is:

1. A manipulator comprising:
an insertion portion configured to be inserted into a body; and
an energy treatment mechanism provided at a distal end of the insertion portion, wherein the energy treatment mechanism comprises:
a first gripping piece;
a second gripping piece supported by the first gripping piece so as to pivot about a pivot axis perpendicular to a longitudinal axis of the insertion portion; and
an energy applying part configured to apply energy to body tissue gripped by the first gripping piece and the second gripping piece,
the insertion portion comprises:
an energy transfer part configured to transfer energy to the energy applying part; and
a force amplifying mechanism configured to amplify a gripping force of the first gripping piece and the second gripping piece,
the force amplifying mechanism comprises:
a pulling pulley supported by the second gripping piece so as to rotate about a pulling rotational axis parallel to the pivot axis, the pulling rotational axis being disposed to be offset proximally from the pivot axis;
an adjustment pulley supported by the insertion portion so as to rotate about an adjustment rotational axis parallel to the pulling rotational axis, the adjustment rotational axis being disposed to be offset proximally from the pulling rotational axis; and
a wire wound around the pulling pulley and the adjustment pulley, wherein one end of the wire is fixed to the insertion portion, and a pulling force applied to the other end of the wire produces tensions of almost the same magnitudes at both sides of the pulling pulley between which the pulling rotation axis is sandwiched,
wherein the pulling pulley is disposed at a position so that a resultant force of the tensions acting on the pulling rotational axis produces a rotational moment that cause the second gripping piece to pivot.

2. A manipulator according to claim 1, wherein the energy transfer part is disposed away from the force amplifying mechanism in a width direction of the insertion portion.

3. A manipulator according to claim 2, wherein the energy transfer part is bent in a crank shape so as to avoid the force amplifying mechanism.

4. A manipulator according to claim 1, wherein the energy transfer part is disposed at a position shifted with respect to the force amplifying mechanism so as not to overlap in the axial direction of the force amplifying mechanism.

5. A manipulator according to claim 1, wherein the energy transfer part comprises an expansion and contraction section that expands and contracts in the longitudinal direction of the insertion portion in accordance with a gripping operation of the first and second gripping pieces.

6. A manipulator according to claim 1, wherein the energy applying part is disposed on a gripping surface of at least one of the first and second gripping pieces.

7. A manipulator according to claim 1, wherein the energy applying part is formed into a sheet shape extending along the longitudinal direction of the insertion portion.

8. A manipulator according to claim 1, wherein the insertion portion is provided with a flexible part.

* * * * *